(12) United States Patent
Nishimura et al.

(10) Patent No.: US 7,985,874 B2
(45) Date of Patent: Jul. 26, 2011

(54) POLYMER PARTICLE

(75) Inventors: Shinichiro Nishimura, Hokkaido (JP); Hideyuki Shimaoka, Tokyo (JP)

(73) Assignee: Sumitomo Bakelite Company, Ltd., Tokyo (JP)

( * ) Notice: Subject to any disclaimer, the term of this patent is extended or adjusted under 35 U.S.C. 154(b) by 873 days.

(21) Appl. No.: 10/594,182

(22) PCT Filed: Mar. 18, 2005

(86) PCT No.: PCT/JP2005/004929
§ 371 (c)(1),
(2), (4) Date: Jul. 5, 2007

(87) PCT Pub. No.: WO2005/097844
PCT Pub. Date: Oct. 20, 2005

(65) Prior Publication Data
US 2008/0254998 A1 Oct. 16, 2008

(30) Foreign Application Priority Data
Mar. 31, 2004 (JP) ................................. 2004-102236
Mar. 31, 2004 (JP) ................................. 2004-102237

(51) Int. Cl.
*C01B 21/14* (2006.01)
(52) U.S. Cl. ........... 560/155; 531/412; 506/20; 536/127
(58) Field of Classification Search .................. None
See application file for complete search history.

(56) References Cited

U.S. PATENT DOCUMENTS
5,449,816 A * 9/1995 Bauer et al. .................... 560/157
2003/0105060 A1 6/2003 Esnault et al.

FOREIGN PATENT DOCUMENTS
| EP | 0648739 B1 | 10/1994 |
| EP | 2004-264027 | 9/2004 |
| JP | 58-069232 | 4/1983 |
| WO | WO-97/33896 | 9/1997 |
| WO | WO 98/29376 | * 7/1998 |
| WO | WO-98/47000 | 10/1998 |
| WO | 01/40796 A2 | 6/2001 |

OTHER PUBLICATIONS

Flitsch, Sabine, et al.; "Sugars Tied to the Spot"; Nature; vol. 421; Jan. 16, 2003; pp. 219-220.
Feizi, Ten, et al.; "Carbohydrate Microarrays- a New Set of Technologies at the Frontiers of Glycomics"; Current Opinion in Structural Biology; Oct. 2003; pp. 637-645.
Seibutsuga, T.; "Acquired Glycosylation Changes in Human Disease"; Chapter 31-37, "Genetic Disorders of Glycosylation in Cultured Cells"; pp. 469-580, Cold Spring Harbor Maruzen Co. Ltd 2003 (originally in Japanese).
Supplementary European Search Report dated Jan. 27, 2011 for Application No. EP 05 72 1116.

* cited by examiner

*Primary Examiner* — Christopher M Gross
(74) *Attorney, Agent, or Firm* — Smith, Gambrell & Russell, LLP

(57) ABSTRACT

A support comprising functional groups supported therein that specifically react with an aldehyde group of a sugar chain, and a polymer particle and a glycochip to which the support is applied, and uses thereof.

9 Claims, 5 Drawing Sheets

[FIG. 4]
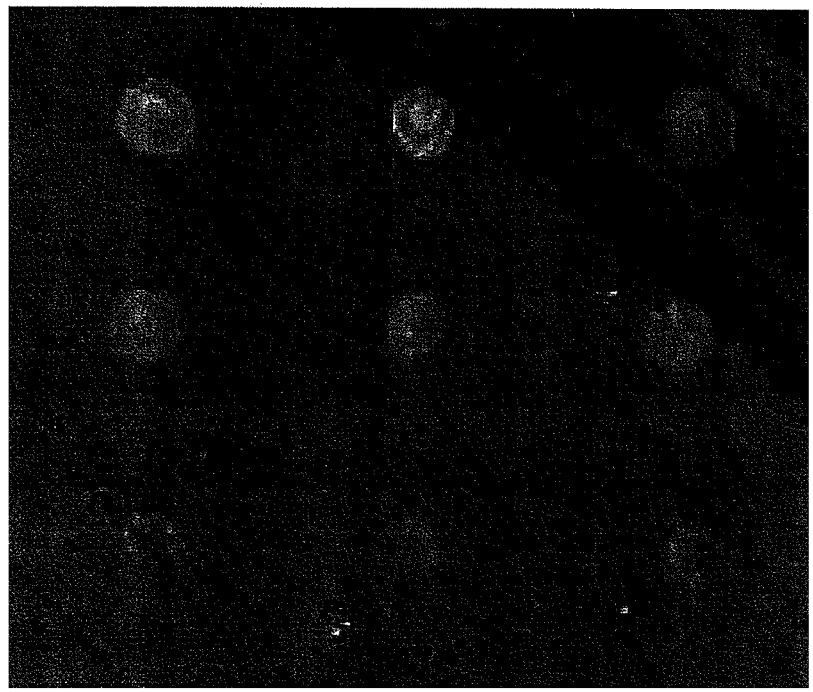
[FIG. 5]
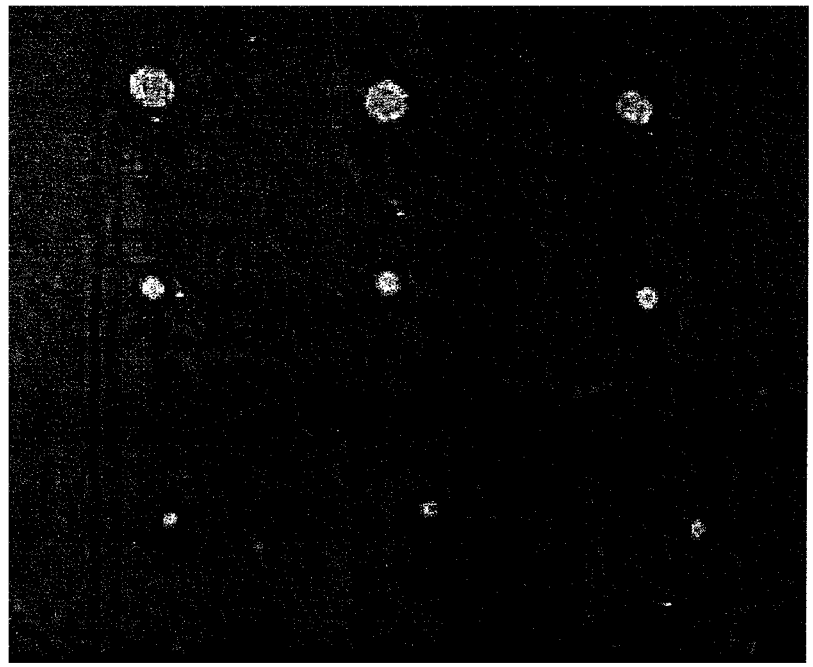

[FIG. 6]
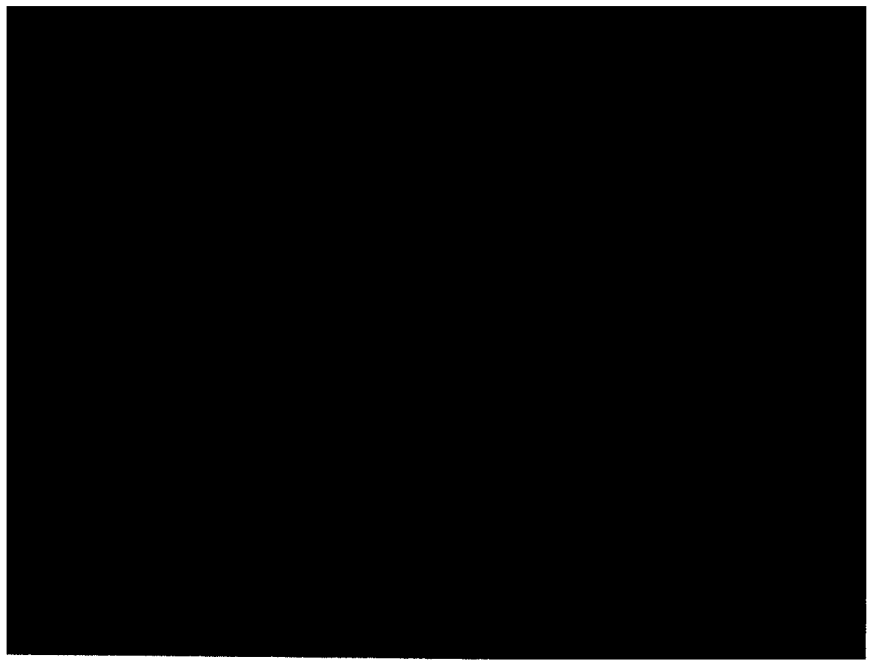

POLYMER PARTICLE

CROSS-REFERENCES TO RELATED APPLICATIONS

This application is a 371 application of International Application No. PCT/JP2005/004929, filed Mar. 18, 2005.

TECHNICAL FIELD

The present invention relates to a support comprising functional groups supported therein that specifically react with an aldehyde group of a sugar chain, for example, a polymer particle used for separation, purification or concentration of sugar chains and substances containing a sugar chain from a sample contaminated with impurities such as a body tissue. Further, the present invention relates to, for example, a glycochip, which is a device wherein sugar chains or derivatives thereof are immobilized on a solid-phase substrate, and use thereof.

BACKGROUND ART

The "sugar chain" is a generic term of a molecule in which monosaccharides and derivatives thereof bond to each other to form a chain structure via glycoside linkages. The monosaccharide includes glucose, galactose, mannose, fucose, xylose, N-acetylglucosamine, N-acetylgalactosamine, sialic acid and the like.

Sugar chains are very rich in diversity and involved in various functions of naturally occurring organisms. Sugar chains, which frequently occur in vivo as complex carbohydrate bound to protein or lipid, are one of major constituents of a living body. It has been revealed that sugar chains in vivo are deeply involved in intercellular signal transduction, regulation of functions and interactions of proteins, and the like.

As a biological macromolecule containing sugar chains, there may be mentioned, for example, cell wall proteoglycans in plant cells, which contribute to stabilization of cells, glycolipids, which affect differentiation, proliferation, adhesion, movement or other behaviors of cells, glycoproteins, which are involved in intercellular interaction, cell recognition, and the like. There have been gradually unveiled mechanisms in which sugar chains in these macromolecules control sophisticated and accurate biological reactions through acting for, replacing, aiding, enhancing, regulating or inhibiting their functions each other. Further, if roles of sugar chains in differentiated proliferation of cells, cell adhesion, immunity and canceration of cells are clarified, new development can be expected through close connection of glycoengineering with medical science, cell engineering or organ engineering.

As an example of such progress, there may be mentioned that study has been actively pursued on occurrence of diseases caused by malfunction of sugar chains in cell surfaces or abnormal sugar chain-receptor interactions, roles of sugar chains in virus infections such as AIDS, and the like. Furthermore, study on involvement of sugar chains in cell-cell interactions or cell-matrix has become more important for understanding biological reactions (see, for example, Non-patent document 1).

For analysis in such study, there have been developed technologies for structural analysis of sugar chains. These technologies are combinations of steps such as liberation of sugar chains from complex carbohydrates, separation and purification of the sugar chains and labeling of the sugar chains. These steps are very complicated. In particular, the step of separation and purification, wherein only sugar chains are recovered from a sample contaminated with impurities, is very difficult and requires highly sophisticated skills.

For separation and purification of sugar chains, there have been used techniques such as ion exchange resins, reverse phase chromatography, activated carbon, and gel filtration chromatography. However, since these techniques are not a method for specifically recognizing sugars, contamination by impurities (such as peptide and protein) may not be avoided, and in many cases recovery efficiency of sugar chain varies depending on its structure. Furthermore, when sugar chains are separated by chromatography with a high degree of accuracy, fluorescence labeling, such as pyridylamination, of the sugar chains is necessary, which requires a complicated operation. In order to analyze the fluorescence-labeled sugar chains, it is necessary to purify the labeled sugar chains by removing impurities such as unreacted 2-aminopyridine from the reaction solution after labeling.

In general, the impurities are removed by gel filtration with the use of the molecular weight difference between the labeled sugar chains and the impurities. However, this method is difficult to treat a large number of samples in short period because it uses many instruments and requires much time. Although removing the impurities by azeotropic distillation has been attempted as a simple method, it is difficult to sufficiently remove the impurities. In order to clarify the relationship between sugar chain structures and various diseases, it is required to investigate sugar chain structures of a large number of samples so that data can be statistically treated. In this case, use of complicated techniques like conventional methods would require huge amount of cost and time. Consequently, there has been demanded a means to separate and purify sugar chains by a simple operation.

Moreover, in analyzing sugar chains involved in various biological reactions, a biochip may be a powerful tool.

Here, the biochip is one of biochemical techniques detecting specific interactions by immobilizing biological substances such as nucleic acids, proteins and sugar chains or cells on a substrate and contacting the immobilized substances or the like (referred to as probe) with biological substances or other compounds (referred to as target), specialized for enabling high-throughput detection/analysis through performing a large number of interactions in parallel. There may be specifically mentioned a DNA chip (DNA microarray), which has been already widely used in the field of function analysis of genes, a protein chip, which is expected to be used in the future, and the like. The DNA chip is a chip wherein nucleic acids are immobilized on its substrate at a high density and the presence of their complementary sequences is detected through hybridization. The protein chip is a chip wherein proteins are immobilized and proteins that interact therewith are detected. A glycochip, wherein sugar chains are immobilized, is expected to greatly contribute to study on interactions between sugar chains and sugar chain receptors, between sugar chains and cells, and between sugar chains and viruses (for example, Non-patent documents 2 and 3). Furthermore, the glycochip is expected to be used as a diagnostic device for infectious diseases and diseases related with sugar chain abnormality. However, there has been no means to immobilize sugar chains on a substrate efficiently by a simple operation, and thus a method to solve this problem has been desired.

[Non-patent document 1] Cold Spring Harbor, Tousa Seibutsugaku, Maruzen Co., Ltd., 2003 (in Japanese); Essentials of Glycobiology, ed. by Ajit Varki, Cold Spring Harbor Laboratory Press, 2002.

[Non-patent document 2] Nature, 2003, vol. 421, pp. 219-220.

[Non-patent document 3] Current Opinion in Structural Biology, 2003, vol. 13, pp. 637-645.

DISCLOSURE OF THE INVENTION

Accordingly, an object of the present invention is to provide a support useful for study on involvement of sugar chains in biological reactions.

Thus, as one aspect, the present invention has as an object to provide polymer particles for separating and purifying only a sugar chain or a substance containing a sugar chain from a sample containing impurities such as a body tissue by a simple operation.

Furthermore, as another aspect, the present invention has as an object to provide a means for producing a glycochip, which is a device wherein sugar chains are immobilized on a substrate, by a simple and efficient method.

The present invention is a support comprising functional groups supported therein that specifically react with an aldehyde group of a sugar chain.

Specifically, the present invention provides (A1) a polymer particle, which is used for a carrier for trapping sugar chains, comprising a functional group that specifically reacts with an aldehyde group of a sugar chain on the surface of the polymer particle;

(A2) the polymer particle according to (A1), wherein the functional group that specifically reacts with an aldehyde group of a sugar chain is at least one selected from an oxylamino group, a hydrazide group and a semithiocarbazide group;

(A3) the polymer particle according to (A1), wherein the functional group that specifically reacts with an aldehyde group of a sugar chain is an oxylamino group;

(A4) the polymer particle according to any of (A1) to (A3), which is composed of a polymer obtained by polymerization of monomer(s) having the functional group that specifically reacts with an aldehyde group of a sugar chain or derivative(s) of the monomer(s);

(A5) the polymer particle according to (A4), wherein the monomer(s) having a functional group that specifically reacts with an aldehyde group of a sugar chain include(s) a monomer represented by the following general formula (1) or a derivative of the monomer:

[Formula 1]

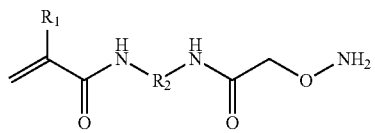

(1)

(wherein $R_1$ represents H or $CH_3$, and $R_2$ represents an arbitrary molecular chain and optionally contains heteroatoms;)

(A6) the polymer particle according to (A4) or (A5), wherein the polymer is a copolymer with monomer(s) that do(es) not react with an aldehyde group of a sugar chain;

(A7) the polymer particle according to (A5), wherein the monomer(s) that do(es) not react with an aldehyde group of a sugar chain include(s) a multifunctional monomer as a crosslinking agent;

(A8) the polymer particle according to any of (A4) to (A7), wherein the polymerization is performed by suspension polymerization;

(A9) the polymer particle according to any of (A4) to (A7), wherein the polymerization is performed by emulsion polymerization;

(A10) the polymer particle according to any of (A1) to (A9), wherein the shape of the polymer particle is spherical;

(A11) the polymer particle according to (A10), wherein the average particle size is 0.05 to 200 µm; and (A12) a method for purifying sugar chains comprising a step of trapping the sugar chains using the polymer particle according to any of (A1) to (A11) and a step of separating the sugar chains.

Specifically, the present invention provides (B1) a glycochip comprising sugar chains immobilized on at least part of a substrate, wherein functional groups that specifically react with an aldehyde group of a sugar chain have been introduced in advance onto the substrate and sugar chains are immobilized via the functional groups;

(B2) the glycochip according to (B1), wherein the functional group is at least one selected from an oxylamino group, a hydrazine group and a semithiocarbazide group;

(B3) the glycochip according to (B1), wherein the functional group is an oxylamino group;

(B4) the glycochip according to any of (B1) to (B3), wherein the introduction of the functional group onto the substrate is performed by coating the substrate surface with a substance having the functional group;

(B5) the glycochip according to (B4), wherein the coating the substrate surface with the substance having the functional group is formation of a molecular membrane on the substrate surface by the Langmuir-Blodgett method;

(B6) the glycochip according to (B4) or (B5), wherein the substance having the functional group is a polymer;

(B7) the glycochip according to (B6), wherein the polymer contains a monomer unit represented by the following general formula (1):

[Formula 2]

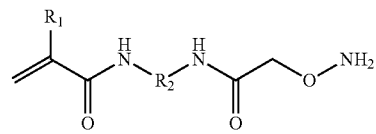

(1)

(wherein $R_1$ represents H or $CH_3$, and $R_2$ represents an arbitrary molecular chain and optionally contains heteroatoms;)

(B8) the glycochip according to any of (B1) to (B3), wherein the introduction of the functional groups onto the substrate is performed via a different functional group that has been introduced onto the substrate in advance;

(B9) the glycochip according to (B8), wherein the introduction of the functional group onto the substrate is performed by reaction of an amino group that has been introduced onto the substrate in advance with a substance having both an oxylamino group and a carboxyl group;

(B10) the glycochip according to (B9), wherein the substance having both an oxylamino group and a carboxyl group is a substance represented by the following formula (2):

[Formula 3]

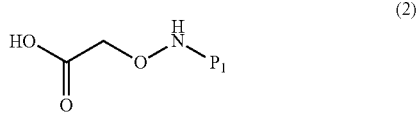

(2)

(wherein $P_1$ represents an arbitrary protecting group;)

(B11) the glycochip according to any of (B1) to (B10), wherein the substrate is made of plastics;

(B12) the glycochip according to any of (B1) to (B11), wherein the aldehyde group of a sugar chain is originated from the reduced terminal of the sugar chain;

(B13) the glycochip according to any of (B1) to (B11), wherein the aldehyde group of a sugar chain is an aldehyde group that was introduced by periodate oxidation or an enzymatic treatment, which is exemplified by treatment with galactose oxidase, of the sugar chain;

(B14) a method of using a glycochip wherein a sample solution is developed onto the glycochip according to any of (B1) to (B13) and interactions between substances contained in the sample and the sugar chains immobilized on the substrate are quantified;

(B15) the method of using a glycochip according to (B14), wherein the substance contained in the sample solution is at least one selected from blood, serum, cell homogenates, proteins, nucleic acids, enzymes, lectins, peptides, peptide nucleic acids, antibodies, sugar chains, glycoproteins, glycolipids and derivatives thereof;

(B16) the method of using a glycochip according to (B14) or (B15), wherein the interactions are quantified by signal detection of fluorescent light; and (B17) a method of using a glycochip wherein cells are seeded on the glycochip according to any of (B1) to (B13) and at least one behavior selected from differentiation, proliferation, adhesion and mutation of cells is controlled with use of interactions between the sugar chains and the cells.

The present invention can provide a support useful for studying involvement of sugar chains in biological reactions.

When the support relating to the present invention is applied to a polymer particle, sugar chains or substances containing a sugar chain can be separated and purified by a simple operation without any complicated steps such as fluorescent labeling and chromatographic purification. The polymer particle of the present invention may be used as packed in a column or the like, thereby facilitating purification of sugar chains to be automated and/or to be sequentially operated.

Furthermore, when the support according to the present invention is applied to a glycochip, sugar chains can be immobilized through a covalent bond on a substrate and, therefore, a highly reliable glycochip suitable for practical use can be provided. The glycochip produced by the method according to the present invention can be used; for example, for studying interactions between sugar chains and receptors, between sugar chains and cells and between sugar chains and viruses, and further it can be used as a research or diagnostic device for infectious diseases or diseases related to abnormality in sugar chains.

BRIEF DESCRIPTION OF THE DRAWINGS

The above-mentioned objects, other objects, features and benefits are revealed by the following suitable embodiments and the accompanying drawings below.

[FIG. 4] shows analytical results for a glycochip of Experimental Example B2 with a microarray scanner.

[FIG. 5] shows analytical results for a glycochip of Experimental Example B3 with a microarray scanner.

[FIG. 6] shows analytical results for a glycochip of Experimental Example B4 with a microarray scanner.

BEST MODE FOR CARRYING OUT THE INVENTION

Figure 1:
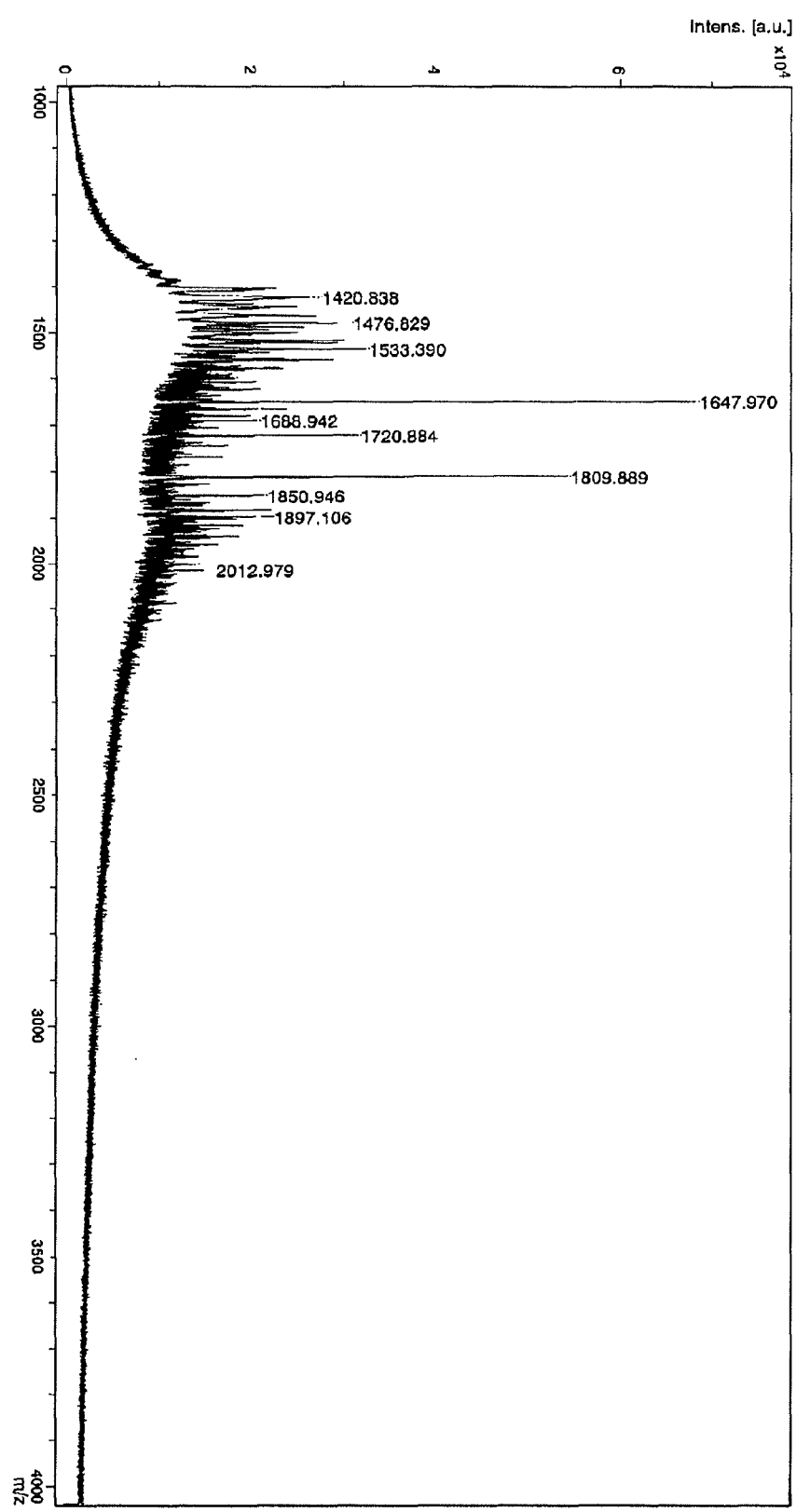
[FIG. 1] shows analytical results for a sugar chain sample of Experimental Example A4 with MALDI-TOF-MS.

Hereinafter, embodiments of the present invention are explained.

(Support)

A support of the embodiments of the present invention supports a functional group that specifically reacts with an aldehyde group of a sugar chain.

(Functional Group that Specifically Reacts with a Sugar Chain)

A sugar chain is the only substance that has an aldehyde group among substances in bodies. That is, in an aqueous solution, a sugar chain is present in an equilibrium between a cyclic hemiacetal form and an acyclic aldehyde form. No aldehyde group is contained in substances in bodies other than sugar chains such as proteins, nucleic acids and lipids. From this fact, if a functional group that specifically reacts with an aldehyde group to form a stable bond is used, only sugar chains can be selectively trapped or immobilized.

As the functional group that specifically reacts with an aldehyde group, there may be mentioned, for example, an oxylamino group, a hydrazide group, an amino group, a semi-thiocarbazide group and derivatives thereof, among which an oxylamino group is preferable. Since an oxime bond formed by a reaction of an oxylamino group with an aldehyde group is readily cleaved by acid treatment or the like, after a sugar chain is trapped by a carrier, the sugar chain can be easily liberated from the carrier, while this oxime bond is known to be stable in a pH region around neutral.

Although, in general, an amino group is frequently used for trapping or supporting physiological active substances, a bond (a Schiff base) generated by a reaction of an amino group and an aldehyde group has a weak binding force, and therefore a secondary treatment using a reducing agent or the like is required. Thus, in consideration of performing various treatments of trapped or immobilized sugar chains, an oxylamino group can be used more preferably than an amino group.

(Application to Polymer Particles)

The aforementioned support can be made in a particulate form and used as a polymer particle. This polymer particle can be preferably used as a carrier for trapping sugar chains.

(Properties of a Polymer Particle)

A polymer particle used for a carrier for trapping sugar chains (hereinafter, abbreviated as a trapping carrier) is preferably a solid particle or a gel particle having a functional group on at least part of its surface that specifically reacts with an aldehyde group of a sugar chain. Thus, through making the polymer particles in a solid particle state or in a gel particle state, after sugar chains are trapped by the polymer particles, the polymer particles trapping the sugar chains can be readily collected by centrifugation, filtration or other methods. In addition, the polymer particles may be loaded into a column.

Such usage is particularly important from the viewpoint of enabling sequential operation.

The shape of the polymer particle is, although not specifically limited, preferably spherical, or being close to spherical. When the polymer particle is spherical, the average particle size is preferably 0.05 to 1000 μm, more preferably 0.05 to 200 μm, further more preferably 0.1 to 200 μm, and most preferably 0.1 to 100 μm. If the average particle size is too small, application of a high pressure is required because of the poor liquid permeability in using the particle as packed in a column, and it is also difficult to collect the polymer particles by centrifugation or filtration. Meanwhile, if the average particle size is too large, the contacting area of the polymer particles with a sample solution is small, thereby reducing the trapping efficiency of sugar chains. Accordingly, a sugar chain trapping carrier which is excellent in the balance of the above-mentioned properties can be provided when the average particle size of the polymer particles is within the above-mentioned range.

The polymer particles may be in a solid particle form or a gel particle form only when collected by centrifugation, filtration or other methods. Specifically, there may be adopted, for example, a method in which a polymer whose solubility varies with changes in environmental conditions such as temperature and pH is used. In the method, after the polymers which are dissolved in a solvent trap sugar chains via the functional group that specifically reacts with an aldehyde group of a sugar chain, the polymers are precipitated by changing their solubilities for collection. As a polymer whose solubility varies depending on environmental conditions includes, for example, poly(N-isopropylacrylamide). By introducing a functional group that specifically reacts with an aldehyde group of a sugar chain into at least part of a poly(N-isopropylacrylamide) molecule, trapping sugar chains can be carried out while changing the solubility of the sugar chain trapping carrier depending on environmental conditions.

(Production of a Polymer Particle)

The above-mentioned polymer particles suitably used as the support of the present embodiments can be produced in large quantities.

The polymer particles can be produced, for example, by polymerizing a monomer having a functional group that specifically reacts with an aldehyde group of a sugar chain or a derivative of such a monomer. The monomer is preferably a vinyl-type monomer containing a vinyl group in the molecule. For example, there may be preferably used derivatives of methacrylic acid, derivatives of acrylic acid, derivatives of styrene, derivatives of propylene and derivatives of acrylamide, among which derivatives of methacrylic acid are more preferred. Furthermore, it is preferable that the functional group that specifically reacts with an aldehyde group of a sugar chain, preferably an oxylamino group, is contained as a side chain in the monomer molecule. The oxylamino group may be protected by a protecting group such as a t-butoxycarbonyl (BOC) group and a 9-fluorenylmethyloxycarbonyl (Fmoc) group. A spacer molecular chain may be also present between the oxylamino group and the vinyl group in the monomer molecule. In particular, if a spacer molecular chain containing heteroatom(s) such as an oxygen atom is present, the environment surrounding the oxylamino group becomes hydrophilic, and a polymer particle obtained by polymerizing such a monomer is especially preferable because the affinity to sugar chains is enhanced in the vicinity of the oxylamino group.

Such a compound includes, for example, compounds represented by the following formula (1):

[Formula 4]

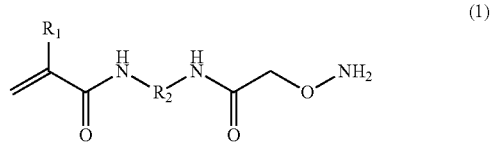

(1)

(wherein $R_1$ represents H or $CH_3$ and $R_2$ represents an arbitrary molecular chain and optionally contains heteroatom(s).)

The polymer may be a homopolymer of a monomer having a functional group that specifically reacts with an aldehyde group of a sugar chain, for example, an oxylamino group, or may be a copolymer of such a monomer and (an)other kind(s) of monomer(s) that do(es) not react with an aldehyde group of a sugar chain, for example, acrylic acid, methacrylic acid, acrylamide, styrene or derivative(s) thereof not having a functional group that reacts with an aldehyde group of a sugar chain. Furthermore, it is preferable that the polymer is obtained by heterogeneous polymerization such as suspension polymerization, emulsion polymerization and the like from the viewpoint of obtaining the polymer in a particulate state.

At this time, the rigidity of the particles can be adjusted by copolymerizing a multifunctional monomer as a crosslinking agent. As the crosslinking agent, there may be used a divinyl compound, for example, ethylene glycol dimethacrylate, divinylbenzene and methylenebisacrylamide as appropriate. The physical properties of the polymer particles can be also controlled by changing the chain length in the molecule of the crosslinking agent to be copolymerized.

Further, a monomer other than a crosslinking agent may be copolymerized. At this time, the density of oxylamino groups in the polymer may be controlled through changing the component ratio in copolymerization by adjusting the amount of each monomer added. Controlling the density of oxylamino groups is important from the viewpoint of optimizing the trapping efficiency of sugar chains.

Besides the method of polymerizing a monomer having a functional group that specifically reacts with an aldehyde group of a sugar chain, as method for obtaining the above-mentioned polymer particles, there may be used a method in which a functional group that specifically reacts with an aldehyde group of a sugar chain is introduced by grafting via another functional group in a side chain contained in a polymer which does not have a functional group that specifically reacts with an aldehyde group of a sugar chain.

(Purification Method of Sugar Chains)

Sugar chains can be purified by carrying out a step of trapping the sugar chains and a step of separating the sugar chains by using the polymer particles obtained in the above-mentioned way. Hereinafter, as the purification method of sugar chains, there is explained a method of selectively recovering only sugar chains by contacting a biological sample containing the sugar chains with the polymer particles, in which the biological sample has been liberated from a sample such as serum, tissue fragments and cells by an enzymatic method such as glycopeptidase digestion or a chemical method such as hydrazinolysis.

(Sugar Chain Trapping)

In the step of sugar chain trapping, only sugar chains in a biological sample are supported on the polymer particles by bonding the functional group that specifically reacts with an aldehyde group of a sugar chain contained in the polymer particles and an aldehyde group of the sugar chains.

Specifically, the polymer particles and sugar chains in a biological sample are brought into contact with each other in a buffer solution of a given pH. The pH of the buffer solution that provides a reaction system for sugar chain trapping is preferably 2 to 9, more preferably 2 to 7, and further more preferably 2 to 6. Various buffer solutions may be used to adjust the pH. The temperature of the reaction system for sugar chain trapping is preferably 4 to 90° C., more preferably 4 to 70° C., more preferably 10 to 70° C., and further more preferably 15 to 60° C. The reaction time may be set as appropriate. Instead of that the polymer particles and the sugar chains are brought into contact with each other in a buffer solution, only the sugar chains may be supported on the polymer particles by passing the solution of the biological sample through a column which is filled with the polymer particles.

(Recovery of Sugar Chains)

Since impurities other than sugar chains are nonspecifically adsorbed on the surface of the polymer particles in the sugar chain trapping, it is preferable to provide a step of washing to remove these impurities before recovering sugar chains. As the washing solution, there may be used water, a buffer solution, an aqueous solution or a buffer solution containing a surfactant, an organic solvent and the like, which may be in combination if necessary. An especially suitable embodiment is a method in which the polymer particles are sufficiently washed with an aqueous solution or a buffer solution which contains a surfactant, then washed with an organic solvent and finally washed with water. All the nonspecific adsorbates are substantially removed from the polymer particles with these washings. When sugar chains are trapped by using a column, the polymer particles may be washed by passing these solutions through the column.

After the sugar chains are trapped by the polymer particles and the polymer particles are washed if necessary, the sugar chains can be liberated and recovered by cleaving the bonds between the polymer particles and the sugar chains. For example, in the case of a polymer particle having an oxylamino group as a functional group that specifically reacts with an aldehyde group of a sugar chain, the bond with the sugar chains can be cleaved by acid treatment or the like because this bond is an oxime bond. From the above view point, a 0.1 to 10% (v/v) aqueous solution of trifluoroacetic acid may be suitably used to liberate the sugar chains from the polymer particles. Alternatively, the sugar chains may be cleaved by a method other than acid treatment. When sugar chains are trapped by using a column, the sugar chains can be eluted by passing a buffer solution which is suitable for given elution conditions through the column.

The sugar chains recovered by this method are purified to such an extent that they are not contaminated with impurities such as proteins, peptides and nucleic acids. Thus, they can be characterized by analytical means such as mass spectrometry, nuclear magnetic resonance analysis and immunoassay, as prepared.

As mentioned above, sugar chains may be purified by carrying out the following operations with using the polymer particle of the present invention; 1) dispersing and reacting the sample solution and the polymer particles to support the reactant on the polymer particle through the functional group that specifically reacts with an aldehyde group of a sugar chain; 2) washing to remove impurities nonspecifically bound to the surface of the polymer particles if necessary; and 3) cleaving the bond between the sugar chains and the polymer particles to recover the sugar chains. Thus, a simple sugar chain purification compared to the conventional methods can be realized. Moreover, the polymer particle of the present invention can be produced in large quantities and has an advantage considering industrial applicability.

(Application to Glycochip)

When the above-described support is provided as part of a substrate, the resultant substrate can be used as a glycochip. In the glycochip, sugar chains are immobilized on the substrate through bonding to at least part of functional groups that specifically react with an aldehyde group of a sugar chain, which are contained in the part corresponding to the support.

(Embodiments of Glycochip)

The glycochip in the present embodiments means a device in which sugar chains, sugar chain derivatives, substances containing sugar chains or the like (hereinafter, unless otherwise specified, mentioned as "sugar chains") are covalently immobilized on a solid-phase substrate.

The solid-phase substrate may be flat plate shape or another shape, for example, the above-mentioned particulate shape, flat plate shape with grooves, porous form, hollow filament shape or the like. The solid-phase support may be a flat plate with partitions like a microtiter plate.

Usually, sugar chains may be immobilized either on part or on the whole of the support comprising the substrate. One kind or a plurality of kinds of sugar chains may be immobilized. As a preferable embodiment, there is mentioned an embodiment in which a plurality of kinds of sugar chains are immobilized in an array on a surface of a flat planar substrate (so-called microarray). As another preferable embodiment, there is mentioned an embodiment in which one or more kinds of sugar chains are immobilized on the whole surface of a substrate, as exemplified by an embodiment in which sugar chains are immobilized on the whole surface of inside walls of each well in a microtiter plate.

(Production of a Substrate for a Glycochip)

The substrate for the glycochip is preferably made of plastics from the viewpoint of feasibility in mass production and various surface treatments. When fluorescence is used as a measurement means, low fluorescent plastics are preferable and, for example, a saturated cyclic polyolefin may be suitably used.

As mentioned above, it is required to introduce functional groups that specifically react and bond with sugar chains to the surface of the substrate for the glycochip. For introducing such functional groups, there are mentioned methods, which are broadly classified in two types: (1) a method wherein a support having such functional groups is formed on the substrate surface by coating the substrate surface with a substance having a functional group that specifically reacts with a sugar chain and (2) a method wherein such functional groups are introduced via different functional groups that have been introduced in advance to the substrate. Hereinafter, each of these methods is described in detail.

(1) Coating the Substrate Surface with the Substance Having the Functional Group A polymer is preferable as the substance having the functional group. The polymer can be produced by polymerizing a monomer having a functional group that specifically reacts with an aldehyde group of a sugar chain, like the above-mentioned polymer particle. The monomer preferably is a vinyl-type monomer containing a vinyl group in the molecule. For example, there may be preferably used derivatives of methacrylic acid, derivatives of acrylic acid, derivatives of styrene, derivatives of propylene, derivatives of acrylamide and the like, among which derivatives of methacrylic acid are more preferred. Moreover, it is preferable that the functional group that specifically reacts with an aldehyde group of a sugar chain, preferably an oxylamino group, is contained as a side chain in the monomer molecule. The oxylamino group may be protected by a protecting group such as a t-butoxycarbonyl (BOC) group and a 9-fluorenylmethyloxycarbonyl (Fmoc) group. A spacer molecular chain may be also present between the oxylamino group and the vinyl group in the monomer molecule. Particularly, if there is a spacer molecular chain containing heteroatom(s) such as an oxygen atom, the environment surrounding the oxylamino group becomes hydrophilic. A polymer obtained by polymerizing such a monomer is especially preferable because the affinity to sugar chains is enhanced in the vicinity of the oxylamino group. As such a compound, there is mentioned a compound represented by the above formula (1).

The polymer may be a homopolymer of a monomer having a functional group that specifically reacts with an aldehyde group of a sugar chain, for example, an oxylamino group, or may be a copolymer of this monomer and (an) other kind(s) of monomer(s) that do(es) not react with an aldehyde group of a sugar chain. Such another monomer includes, for example, acrylic acid, methacrylic acid, acrylamide and styrene, and derivatives thereof which do not have a functional group that reacts with an aldehyde group of a sugar chain. Besides this method, there may be used a method wherein a functional group is introduced into a polymer by the above-mentioned graft reaction.

As a preferable embodiment of the coating, there may be used a general method such as dip-coating method, casting method, spin-coating method and the like as appropriate. The concentration of the polymer solution used for coating is preferably 0.01 to 10% by weight, more preferably 0.01 to 5% by weight, further more preferably 0.01 to 2% by weight. As another method, there may be used a method of forming a monomolecular membrane on the substrate surface by the Langmuir-Blodgett method. When, for example, an oxylamino group is used as a functional group that reacts with an aldehyde group of a sugar chain and the oxylamino group is protected by a given protecting group, the substance is provided for coating after being subjected to a suitable deprotecting treatment.

In this way, by forming a support having functional groups that specifically react with an aldehyde group of a sugar chain on the substrate surface, the functional groups that specifically react with the sugar chain can be introduced onto the substrate.

(2) Introduction of the Functional Group Via a Different Functional Group Introduced in Advance onto a Substrate This is a method wherein a first functional group is introduced in advance onto the substrate surface and then a second functional group that can bond a sugar chain is introduced via the first functional group. As the first functional group, there are mentioned an amino group, a carboxyl group, a hydroxyl group and the like. As method for introducing the first functional group, there may be used plasma exposure, coating with an alkoxysilane containing the first functional group, surface graft polymerization of a monomer containing the first functional group, and the like as appropriate.

Next, after the first functional group was introduced, the second functional group is introduced via the first functional group by a reaction between a substance which contains both the second functional group and a functional group that can react with the first functional group, and the first functional group. As a specific example, here is explained the case in which an amino group is introduced as the first functional group and an oxylamino group as the second functional group. By treating the first functional group on the substrate surface with a compound (molecule) having both an oxylamino group and a carboxyl group, a condensation reaction between the amino group and the carboxyl group takes place, the resultant compound is immobilized on the substrate surface and, as a result, an oxylamino group is introduced on the substrate.

Here, as a molecule having both an oxylamino group and a carboxyl group, there may be used aminooxyacetic acid represented by the following formula (2) and the like. In this case, the oxylamino group may be protected by a protecting group.

[Formula 5]

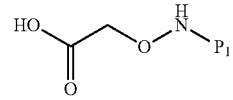

(2)

(wherein P$_1$ represents an optional protecting group.)

Further, the amino group introduced on the substrate as the first functional group can bond to the carboxyl group of the compound of formula (2) through reaction between them in the presence of a condensing agent such as, typically, a carbodiimide compound. When the oxylamino group is protected by a protecting group, the protecting group can be removed through an appropriate deprotecting treatment after the step of introducing the oxylamino group, that is, after the reaction of the compound of formula (2) with the amino group on the substrate.

(Immobilization of Sugar Chains)

Immobilization of a sugar chain onto the substrate is performed by contacting a solution prepared by dissolving the sugar chain with the substrate surface. One of the preferable embodiments is a method of spotting the solution containing the sugar chain in an array on the substrate surface. For spotting, there may be used a spotting system using spotting pins (for example, "SPBIO" series manufactured by Hitachi Software Engineering Co., Ltd.), an inkjet system (for example, "Piezorray" manufactured by Perkin-Elmer, Inc.) and the like as appropriate. The liquid for dissolving sugar chains may be water, a buffer solution or another solvent and may contain an additive other than sugar chains. As the additive, there may be mentioned a surfactant, a macromolecular compound, various kinds of salts and the like. Adding a surfactant is useful for controlling the wettability of the substrate surface with the sugar chain solution. It is preferable that the pH of the sugar chain solution is adjusted to be in a range optimal for reaction of an aldehyde group of a sugar chain with the functional group on the substrate surface. In any of the methods, one kind or a plurality of kinds of sugar chains may be immobilized.

As one of other preferable embodiments, there may be mentioned a method of immersing the substrate in a solution containing sugar chains or developing a solution containing sugar chains on the substrate surface. This method is particularly useful in the case of immobilizing sugar chains on the whole surface of the substrate. If the substrate is provided with partitions like wells of a microtiter plate, a method of dispensing the sugar chain solution to each well is also useful. In any of the methods, one kind or a plurality of kinds of sugar chains may be immobilized.

After immobilizing sugar chains on the substrate, sugar chains that are not immobilized may be removed by washing. Although the conditions such as the washing solution and the washing method may be set as appropriate, it is preferable to use, for example, a buffer solution containing a surfactant, purified water, an organic solvent or the like.

The bond of a sugar chain to the substrate involving immobilization of sugar chain is formed by reaction of an aldehyde group of the sugar chain with the functional group that specifically reacts with sugar chains, for example, an oxylamino group, formed on the substrate.

Here, the aldehyde group of the sugar chain may be an aldehyde group originated from the reducing terminal of the sugar chain or an aldehyde group introduced by other means. An aldehyde group may be introduced into the sugar chain by enzymatic treatment such as oxidation by galactose oxidase treatment and the like. This method can be applied to sugar chains having galactose or N-acetylgalactosamine at the non-reducing terminal and it converts the hydroxymethyl group at the 6-position of galactose into an aldehyde group. Alternatively, an aldehyde group may be introduced by periodate oxidation of a sugar chain through conversion of the end group into an aldehyde.

(Usage of the Glycochip)

As one of the preferable methods for using the glycochip of the present embodiments, there is mentioned a method in which a sample solution is developed on the glycochip and the interactions between the substances contained in the sample solution and the sugar chains on the chip are quantified. This method is the same usage as that of conventional DNA chips or protein chips.

As the sample solution, there is mentioned a solution containing blood, serum, homogenates or extracts of tissues, homogenates or extracts of cells, proteins, nucleic acids, enzymes, lectins, peptides, peptide nucleic acids, antibodies, sugar chains, glycoproteins, glycolipids, derivatives thereof or the like.

It is preferable that, after the sample solution is developed on the chip and the reaction is allowed to proceed for a given period, the unreacted sample is removed by washing. When the sample solution contains a substance that interacts with the sugar chain on the chip, the substance reacts with the sugar chain immobilized on the chip and remains at the binding position (spotting position) even after the washing operation. It is possible to quantify the strength of interaction between the sugar chain and the sample substance by measuring the residual amount. As the means for quantifying the interaction, there may be used, for example, labeling with a fluorescent substance, labeling with a radioactive isotope, color development with various coloring agents, spectroscopic measurements and physical measurements using an atomic force microscope and the like. From viewpoint of easiness of measurement and simplicity of operation, it is preferable that the quantification of the interaction is performed by detecting a fluorescent signal with the use of labeling with a fluorescent substance.

As another preferable method of using the glycochip of the present embodiment, there is mentioned a method in which cells are seeded on the glycochip and the behavior of the cells on the chip are investigated. It is considered that sugar chains influence adhesion, proliferation property, differentiation ability and mutation properties of cells. Accordingly with the use of interactions between sugar chains and the cells, it possible to control at least one of the behaviors selected from differentiation, proliferation, adhesion and mutation of the cells. That is, such use of the glycochip is a useful means for study on ability of cells to recognize sugar chains, cell specific culture, control of differentiation induction for stem cells, and the like.

EXAMPLE 1

Experimental Example A1

(Synthesis of Oxylamine-Containing Monomer)

Reaction of 5 g of methacrylic anhydride (manufactured by Wako Pure Chemical Industries, Ltd.) and 25 g of 2,2'-(ethylenedioxy)bis(ethylamine) was performed in 200 mL of chloroform for 16 hrs. The progress of the reaction was confirmed by thin layer chromatography (TLC). After completion of the reaction, the resultant product was purified by a usual method with silica-gel chromatography and then the solvent was distilled off.

The product was again dissolved in chloroform and to the resultant solution 10 g of Water-Soluble-Carbodiimide (manufactured by Wako Pure Chemical Industries, Ltd.) and 5 g of BOC-aminooxyacetic acid (manufactured by Novabiochem Corp.) were added, and reaction was performed at room temperature for 16 hrs. The progress of the reaction was confirmed by TLC. After completion of the reaction, the resultant product was extracted with purified water 3 times, followed by purification with silica-gel chromatography. The purified product was identified with nuclear magnetic resonance (NMR) analysis and a matrix-assisted laser desorption ionization time-of-flight mass spectrometer (MALDI-TOF-MS, "UltraFlex" manufactured by Bruker Daltonics Inc.). The structural formula of the synthesized monomer is shown in the following formula.

[Formula 6]

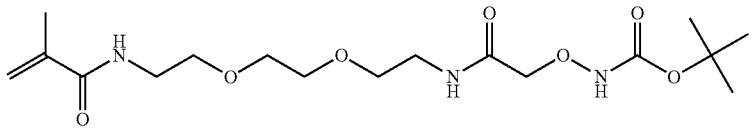

Experimental Example A2

(Synthesis of Polymer Particles)

In 1 mL of chloroform, 1 g of the monomer synthesized in Experimental Example A1 was dissolved and the resultant solution was charged to a reaction vessel equipped with a reflux condenser. To the reaction vessel, there were added 30 mL of purified water and 0.05 g of polyvinyl alcohol (the degree of polymerization: approximately 1500, manufactured by Wako Pure Chemical Industries, Ltd.), and the reaction vessel was set in a thermostat at 65° C. The solution in the reaction vessel was purged with nitrogen for 30 min while stirring. The polymerization reaction was started by injecting a solution prepared by dissolving 0.05 g of 2,2'-azobis(isobutyronitrile) in a quite small amount of chloroform into the reaction vessel. After the reaction was continued for 16 hrs, the reaction vessel was immersed in chilled water to stop the polymerization reaction. The precipitate generated in the reaction vessel was collected by centrifugation, and the resultant precipitate was washed with methanol and purified water each 5 times.

The precipitate after washing was placed in a vessel, and to the vessel a solution prepared by diluting trifluoroacetic acid with methanol by three fold was added in a large excessive amount to the precipitate. The reaction vessel was placed in a thermostat at 40° C. and reaction was performed with shaking for 3 hrs to remove the protecting group (BOC group) bonded to the oxylamino group. After the reaction was completed, the resultant precipitate was collected by centrifugation and washed with methanol and purified water each 5 times to obtain polymer particles. The average particle size of the polymer particles obtained was approximately 10 μm.

Experimental Example A3

(Measurement of Sugar Chain Trapping Ratio using Model Sugar Chain)

A solution was prepared by dissolving 1 mg of N-acetyl-lactosamine (manufactured by Sigma-Aldrich Co.) in 100 μL of purified water. In this solution, 10 mg of the polymer particles prepared in Experimental Example A2 were dispersed. The pH of the resultant solution was adjusted to 2 with a hydrochloric acid buffer solution and the reaction was performed with shaking at 40° C. for 16 hrs. After the reaction, the polymer particles were precipitated with centrifugation and the supernatant was removed. The polymer particles collected were washed with a 0.1% aqueous solution of sodium dodecylsulfate, 50% methanol and purified water each 5 times. After washing, the polymer particles were dispersed in 10% trifluoroacetic acid and the sugar chain was liberated by shaking at room temperature for 3 hrs. The polymer particles were precipitated by centrifugation and the supernatant was collected. The supernatant collected was lyophilized to obtain a sugar chain sample.

The amount of the recovered sugar chain sample was quantified by the orcinol-sulfuric method in accordance with conventional procedures to determine the sugar chain trapping ratio. The results are shown in Table 1. The sugar chain trapping ratio was significantly higher compared to that of Experimental Example 7, which serves as the comparative example (described later), showing that sugar chains can be efficiently recovered by the polymer particles according to the present invention.

Experimental Example A4

(Purification of Sugar Chains from Glycoprotein)

After 50 mg of immunoglobulin G (IgG) from mouse was treated with a protease, N-glycoside type sugar chains were cleaved with N-glycopeptidase F in accordance with a conventional method. To the solution obtained, 10 mg of the polymer particles prepared in Experimental Example A2 were dispersed, the pH of the resultant solution was adjusted to 2, and reaction was performed at 40° C. for 16 hrs. After the reaction was completed, the polymer particles were precipitated by centrifugation and the supernatant was removed. The polymer particles collected were washed with a 0.1% aqueous solution of sodium dodecylsulfate, 50% methanol and purified water each 5 times. After washing, the polymer particles were dispersed in 10% trifluoroacetic acid, and the sugar chains were liberated with shaking at room temperature for 3 hrs. The polymer particles were precipitated by centrifugation and the supernatant was collected. The supernatant collected was lyophilized to obtain a sugar chain sample.

The sugar chain sample obtained was analyzed by MALDI-TOF-MS. 2,5-Dihydroxybenzoic acid was used as a matrix. The measurement result is shown in FIG. 1. The molecular weight peaks assignable to the sugar chains were clearly observed, showing that sugar chains in glycoproteins can be purified and recovered using the polymer particles of the present invention.

Experimental Example A5

Figure 2:
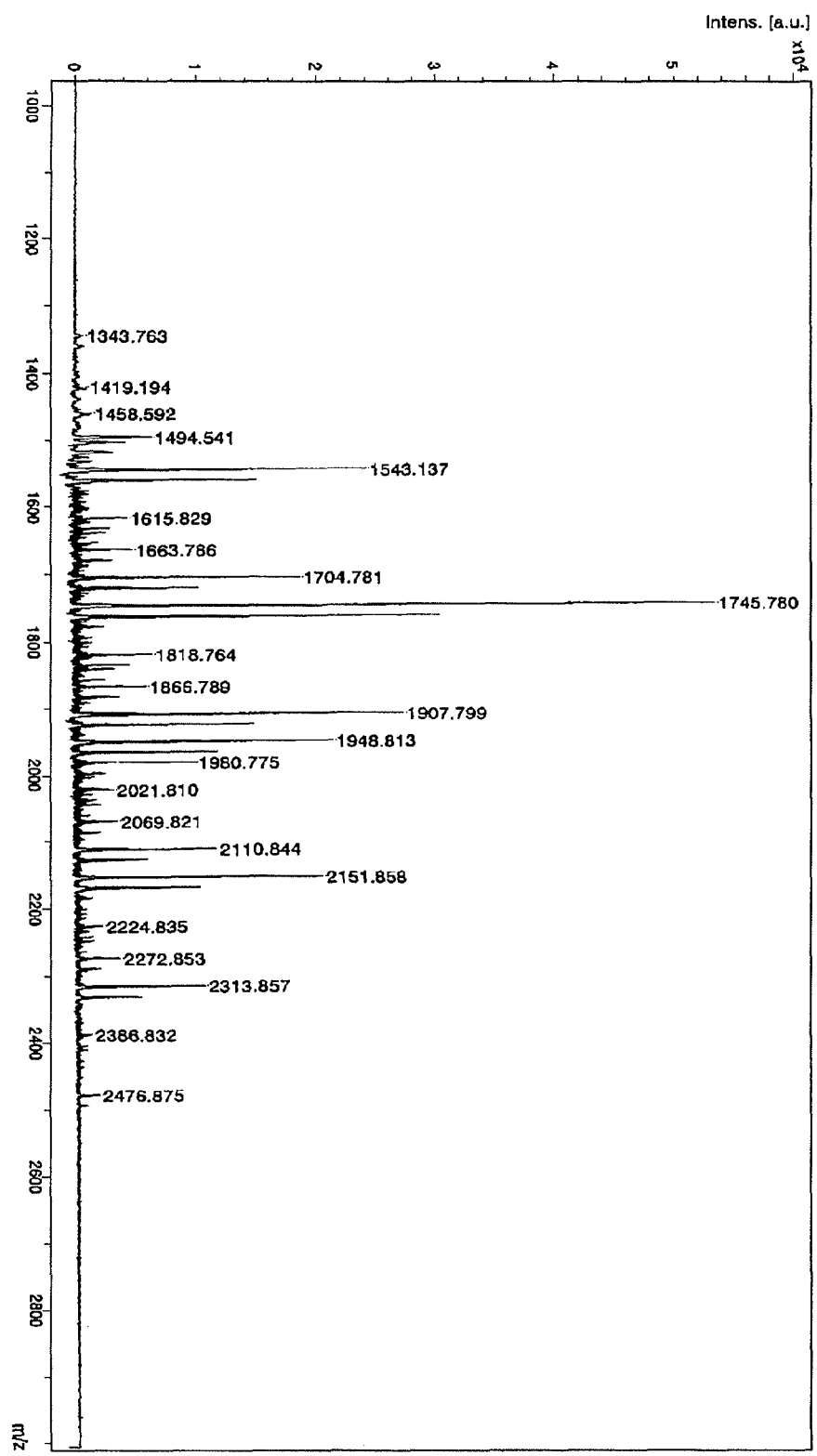
[FIG. 2] shows analytical results for a sugar chain sample of Experimental Example A5 with MALDI-TOF-MS.

Using 50 mg of hen's-white-egg albumin, the sugar chain sample was purified by the same method of Experimental Example A4 and analyzed by MALDI-TOF-MS. The measurement result is shown in FIG. 2. The molecular weight peaks assignable to the sugar chains were clearly observed, showing that sugar chains in glycoproteins can be purified and recovered using the polymer particles of the present invention.

Experimental Example A6

Figure 3:
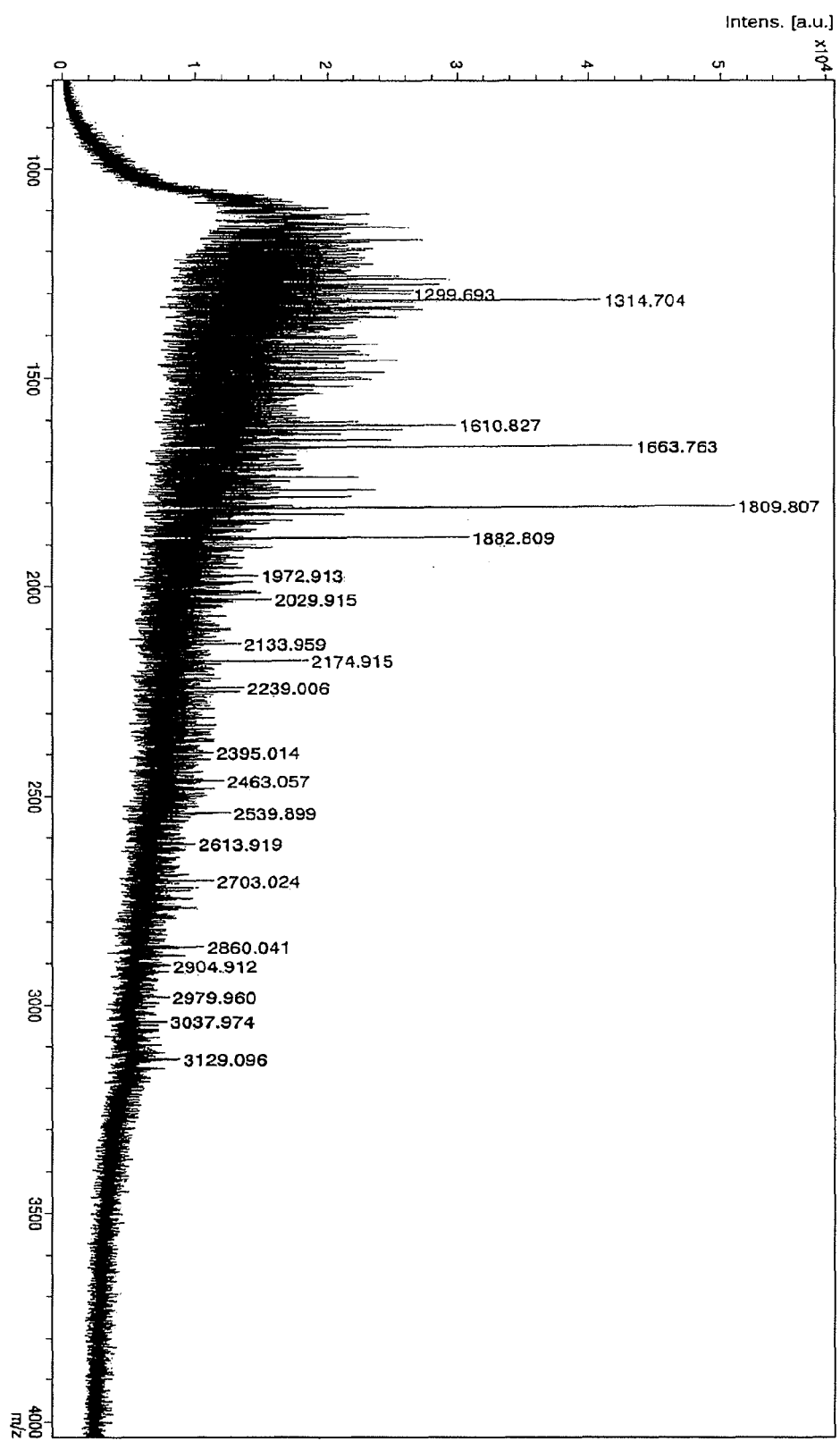
[FIG. 3] shows analytical results for a sugar chain sample of Experimental Example A6 with MALDI-TOF-MS.

A specimen of dermal tissue was taken from mouse skin and fragmented after being defatted with acetone. The sugar chain sample was purified by the same method of Experimental Example A4 and analyzed by MALDI-TOT-MS. The measurement result is shown in FIG. 3. The molecular weight peaks assignable to the sugar chains were clearly observed, showing that sugar chains can be purified and recovered from a biological sample using the polymer particles of the present invention.

Experimental Example A7

(Synthesis of Polymer Particles)

A mixture of 1 g of methyl methacrylate monomer and 1 mL of chloroform was charged to a reaction vessel equipped with a reflux condenser. To the reaction vessel, there were added 30 mL of purified water and 0.05 g of polyvinyl alcohol (the degree of polymerization: approximately 1500, manufactured by Wako Pure Chemical Industries, Ltd.), and the reaction vessel was placed in a thermostat at 65° C. The solution in the reaction vessel was purged with nitrogen for 30 min with stirring. The polymerization reaction was started by injecting a solution prepared by dissolving 0.05 g of 2,2'-azobis(isobutyronitrile) in a small amount of chloroform into the reaction vessel. After the reaction was continued for 16 hrs, the reaction vessel was immersed in cold water to stop the polymerization reaction. The precipitate formed in the reaction vessel was collected by centrifugation and washed with methanol and purified water each 5 times to obtain polymer particles.

(Purification of Sugar Chains)

A solution was prepared by dissolving 1 mg of N-acetyl-lactosamine (manufactured by Sigma-Aldrich Co.) in 100 μL of purified water. In this solution, 10 mg of the polymer particles prepared by the above-mentioned method was dispersed. The pH of the resultant solution was adjusted to 2 with a hydrochloric acid buffer solution, and the reaction was performed with shaking at 40° C. for 16 hrs. After the reaction was completed, the polymer particles were precipitated by centrifugation and the supernatant was removed. The polymer particles collected were washed with a 0.1% aqueous solution of sodium dodecylsulfate, 50% methanol and purified water each 5 times. After washing, the polymer particles were dispersed in 10% trifluoroacetic acid and this mixture was shaken at room temperature for 3 hrs. The polymer particles were precipitated by centrifugation and the supernatant was collected. The supernatant collected was lyophilized to obtain a comparative sample for comparing with the result of Experimental Example A3.

The amount of the sugar chains contained in the recovered sample was quantified by the orcinol-sulfuric method in accordance with the conventional procedure. The results are shown in Table 1. Almost no sugar chain was recovered, indicating that sugar chains can not be purified with the polymer particles that do not contain a functional group specifically reacting with an aldehyde group of a sugar chain.

[Table 1]

TABLE 1

|  | Polymer Particle | Sugar Chain Trapping Ratio |
| --- | --- | --- |
| Experimental Example A3 | Polymer particle containing oxylamino group | 65% |
| Experimental Example A7 | Polymer particle containing no oxylamino group | 5% |

Experimental Example B1

(Preparation of a Polymer Solution)

A reaction vessel equipped with a reflux condenser was charged with 1 g of the monomer synthesized in Experimental Example A1 and 3 g of methyl methacrylate (manufactured by Wako Pure Chemical Industries, Ltd.). To this reaction vessel, 30 mL of chloroform was added and the reaction vessel was set in a thermostat at 65° C. The solution in the reaction vessel was purged with nitrogen while stirring for 30 min. The polymerization reaction was started by adding 0.05 g of 2,2'-azobis (isobutyronitrile) (manufactured by Wako Pure Chemical Industries, Ltd.) into the reaction vessel. After the reaction was continued for 16 hrs, the reaction vessel was immersed in cold water to stop the polymerization reaction, thereby obtaining a polymer solution.

Experimental Example B2

(Preparation of a Substrate)

A saturated cyclic polyolefin resin was molded by an injection molding method to prepare a 1-mm thick substrate of flat plate shape. The surface of this substrate was made hydrophilic by plasma treatment under an oxygen atmosphere.

(Introduction of Oxylamino Groups onto the Substrate Surface)

The above-mentioned substrate was immersed in the polymer solution obtained in Experimental Example B1 and kept for 30 min. After the immersion, the substrate was gently drawn up from the solution and dried at 25° C. for 1 hr. Subsequently, the substrate was immersed in 1 M hydrochloric acid containing 10% acetic acid for 3 hrs, thereby removing the BOC group. The substrate was washed with purified water and air-dried.

(Immobilization of Sugar Chains)

Mannotriose (manufactured by Dextra Laboratories Ltd.) was dissolved in acetate buffer solutions (pH 4, 100 mM) at each of concentrations of 10 mg/mL, 1 mg/mL and 0.1 mg/mL. On the surface of the substrate prepared above, 1 µL of each solution was spotted. The substrate after spotting was placed in a moistened chamber and kept at room temperature for 1 hr. A solution was prepared by dissolving 3% by weight of bovine serum albumin (manufactured by Wako Pure Chemical Industries, Ltd.) in a Tris-HCl buffer (pH 7.4, 10 mM). The substrate kept as described above was immersed in this solution for 1 hr, thereby blocking the substrate surface. After blocking, the substrate was washed with purified water and air-dried.

(Reaction of Lectin)

Rhodamine-labelled concanavalin A (manufactured by Funakoshi Co., Ltd.) was dissolved in a phosphate buffer solution (PBS, pH 7.4, 100 mM) at a concentration of 20 µg/mL. Onto the substrate blocked, 20 µL of this solution was dropped, a cover glass was put thereon, and the substrate was kept at room temperature for 1 hr. After that, the cover glass was removed and the substrate was washed with a washing solution (obtained by dissolving 0.05% by weight of Tween-20 in PBS) 3 times. The substrate was further washed with purified water and air-dried.

(Measurement)

Measurements were performed for the surface of the substrate treated as above by using a microarray scanner "ScanArray LITE" (manufactured by Packard Biochip Technologies, Inc.). The measurement conditions were as follows: laser intensity, 90%; PMT sensitivity, 60%; excitation/detection wavelength, Rhodamine channel. The result of imaging the fluorescence intensity from the substrate surface is shown in FIG. 4. In the figure, the upper 3 spots have a mannotriose concentration of 10 mg/mL, the middle 3 spots have a mannotriose concentration of 1 mg/mL, and the lower 3 spots have a mannotriose concentration of 0.1 mg/mL at the time of spotting, respectively.

The fluorescence intensity was high only on the regions where mannotriose was spotted, indicating that Rhodamine-labelled concanavalin A was bound in these regions. It is known that concanavalin A recognizes and binds to mannose. Consequently, it was shown that mannotriose was immobilized on the substrate.

Experimental Example B3

(Preparation of the Substrate)

A saturated cyclic polyolefin resin was molded by injection molding method to prepare a 1 mm thick substrate of flat plate shape. The substrate surface was made to hydrophilic by plasma treatment under an oxygen atmosphere.

(Introduction of Oxylamino Groups onto the Substrate Surface)

Step 1: 3-Aminopropyltrimethoxysilane was dissolved in purified water at a concentration of 2% by weight. The above substrate was immersed in this solution. The immersion was performed at 25° C. for 1 hr. After the immersion, the substrate was washed with purified water and dried. The substrate was dried in vacuum using a vacuum desiccator with the temperature maintained at 45° C.

Step 2: BOC-Aminooxyacetic acid was dissolved in methanol at a concentration of 2% by weight, and Water-Soluble-Carbodiimide (manufactured by Wako Pure Chemical Industries, Ltd.) was added here in an amount of 1.5 equivalents to BOC-aminooxyacetic acid. The substrate obtained in Step 1 was immersed in this solution. The immersion was performed at 25° C. for 12 hrs. After the immersion, the substrate was washed with methanol and dried. Subsequently, the substrate was immersed in 1 M hydrochloric acid containing 10% acetic acid for 3 hrs, thereby removing a BOC group. The substrate was washed with purified water and air-dried.

(Immobilization of Sugar Chains)

Mannotriose was immobilized on the substrate by the same method as that of Experimental Example B2.

(Reaction of Lectin)

The reaction with Rhodamine-labelled concanavalin A was performed by the same method as that of Experimental Example B2.

(Measurement)

The fluorescence intensity from the substrate surface was measured by the same method as that of Experimental Example B2. The result of imaging the fluorescence intensity from the substrate surface is shown in FIG. 5. In the figure, the upper 3 spots have a mannotriose concentration of 10 mg/mL, the middle 3 spots have a mannotriose concentration of 1 mg/mL, and the lower 3 spots have a mannotriose concentration of 0.1 mg/mL at the time of spotting, respectively.

As the case with Experimental Example B2, the fluorescence intensity was high only on the regions where mannotriose was spotted, indicating that Rhodamine-labelled concanavalin A was bound to these regions. It is known that concanavalin A recognizes and binds to mannose. Consequently, it was shown that mannotriose was immobilized on the substrate.

Experimental Example B4

(Preparation of the Substrate)

A saturated cyclic polyolefin resin was molded by injection molding method to prepare a 1 mm thick substrate of flat plate shape. The substrate surface was made hydrophilic by plasma treatment under an oxygen atmosphere. No treatment for introducing oxylamino groups as performed in Experimental Example B2 was carried out.

(Immobilization of Sugar Chains)

Immobilization of mannotriose on the substrate was performed by the same method as that of Experimental Example B2.

(Reaction of Lectin)

The reaction with Rhodamine-labelled concanavalin A was performed by the same method as that of Experimental Example B2.

(Measurement)

The fluorescence intensity from the substrate surface was measured by the same method as that of Experimental Example B2. The result of imaging the fluorescence intensity from the substrate surface is shown in FIG. 6.

In Experimental Example B4, there was no region where the fluorescence intensity, was high, indicating that there was no region to which concanavalin A specifically bound, which is different from the results in Experimental Examples B2 and B3. That is, it was shown that mannotriose was not immobilized on the substrate.

From Experimental Examples B2 to B4 it was revealed that the presence of oxylamino groups was essential to immobilization of sugar chains.

The invention claimed is:

1. A a polymer particle, wherein the polymer A polymer particle, wherein the polymer particle comprises a polymer obtained by polymerizing a monomer represented by the following general formula (1)

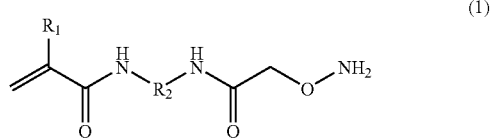

wherein $R_1$ represents H or $CH_3$ and $R_2$ represents a molecular chain and optionally contains heteroatom(s), and wherein the polymer particle specifically reacts with an aldehyde group of a sugar chain.

2. The polymer particle according to claim 1, wherein the polymer is a copolymer of a monomer having functional group (1) and a monomer or monomers that do not react with an aldehyde group of a sugar chain.

3. The polymer particle according to claim 2, wherein the monomers that do not react with an aldehyde group of a sugar chain include a multifunctional monomer as a crosslinking agent.

4. The polymer particle according to claim 1, wherein the polymer is obtained by suspension polymerization method.

5. The polymer particle according to claim 1, wherein the polymer is obtained by emulsion polymerization method.

6. The polymer particle according to claim 1, wherein the particle shape is spherical.

7. The polymer particle according to claim 6, wherein the average particle size is 0.05 to 200 μm.

8. A method for purifying sugar chains comprising steps of:
trapping sugar chains by using the polymer particle according to claim 1; and
separating the sugar chains.

9. The polymer particle according to claim 1 further comprising a support.

* * * * *

UNITED STATES PATENT AND TRADEMARK OFFICE
CERTIFICATE OF CORRECTION

| | | |
|---|---|---|
| PATENT NO. | : 7,985,874 B2 | Page 1 of 1 |
| APPLICATION NO. | : 10/594182 | |
| DATED | : July 26, 2011 | |
| INVENTOR(S) | : Shinichiro Nishimura et al. | |

It is certified that error appears in the above-identified patent and that said Letters Patent is hereby corrected as shown below:

In the Claims

Column 20, lines 8-24 should read,

-- 1. A polymer particle, wherein the polymer particle comprises a polymer obtained by polymerizing a monomer represented by the following general formula (1):

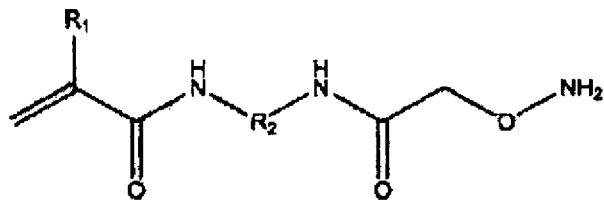

wherein R1 represents H or CH3 and R2 represents a molecular chain and optionally contains heteroatom(s), and wherein the polymer particle specifically reacts with an aldehyde group of a sugar chain. --

Signed and Sealed this
Sixteenth Day of December, 2014

Michelle K. Lee
*Deputy Director of the United States Patent and Trademark Office*